United States Patent [19]

Hama et al.

[11] Patent Number: 4,818,559

[45] Date of Patent: Apr. 4, 1989

[54] METHOD FOR PRODUCING ENDOSSEOUS IMPLANTS

[75] Inventors: Masaaki Hama, Seattle, Wash.; Keiichirou Watanabe, Toyonaka; Hiroshi Ishimaru, Niihama, both of Japan

[73] Assignee: Sumitomo Chemical Company, Limited, Osaka, Japan

[21] Appl. No.: 890,286

[22] Filed: Jul. 29, 1986

[30] Foreign Application Priority Data

Aug. 8, 1985 [JP] Japan .................. 60-175568
Aug. 8, 1985 [JP] Japan .................. 60-175570

[51] Int. Cl.⁴ .................. A01N 1/02; B05D 1/08; B05D 3/00; A61C 8/00
[52] U.S. Cl. .................. 427/2; 427/307; 427/330; 427/423; 427/34; 433/173; 433/201.1; 623/11
[58] Field of Search .................. 427/2, 34, 307, 330, 427/423; 623/11; 433/173, 174, 175, 176, 201.1

[56] References Cited

U.S. PATENT DOCUMENTS

| | | |
|---|---|---|
| 3,643,658 | 2/1972 | Steinemenan . |
| 4,044,170 | 8/1977 | Scharbach et al. .................. 427/2 |
| 4,145,764 | 3/1979 | Suzuki et al. .................. 427/2 |
| 4,146,936 | 4/1979 | Aoyagi et al. . |
| 4,159,358 | 6/1979 | Hench et al. .................. 427/318 |
| 4,206,516 | 6/1980 | Pilliar . |
| 4,626,209 | 12/1986 | Tsai et al. .................. 427/2 |

Primary Examiner—Norman Morgenstern
Assistant Examiner—Marianne L. Padgett
Attorney, Agent, or Firm—Birch, Stewart, Kolasch & Birch

[57] ABSTRACT

An improved method for producing endosseous implants by thermally spraying a ceramic material onto the surface of a metallic core material having a rough surface, i.e. a maximum surface roughness of 15 to 100 μm, which can produce implants which have excellent characteristics in regard to the metallic material and ceramic material and do not dissolve out harmful metal ions. The endosseous implants are useful for implantation in various bones including tooth roots and joints in living bodies.

8 Claims, 1 Drawing Sheet

METHOD FOR PRODUCING ENDOSSEOUS IMPLANTS

The present invention relates to a method for producing endosseous implants, and more particularly, to an improved method for producing endosseous implants without dissolving out metal ions.

BACKGROUND OF THE INVENTION

The implantology which comprises insertion of artificial materials such as artificial organs, artificial blood vessels, artificial joints artificial bones and artificial tooth roots into living bodies so as to recover lost parts of living bodies or their functions has been received much attention in recent years. It is said that a trial of implantation goes back to ancient times. Particularly in the past ten years, a huge number of treatments by implantation have been performed on bones and tooth roots to afford good results in the remedy of the defects or recovery of functions thereof. However, there has not yet been obtained an articial bone or tooth root which satisfies the necessary requirements as the material for living bodies, i.e. affinity to living bodies, safety, excellent durability.

As metallic materials which have mainly been used for preparation of artificial bones or tooth roots, cobalt-chromium alloys, stainless steel, titanium and tantalum are exemplified. On the other hand, as ceramic mterials, alumina or materials comprising predominantly carbon have been recently taken note of.

Although metallic materials are excellent in mechanical strength, particularly in impact strength, they are faulty in their affinity to tissues of living bodies. For example, when a metallic implant is used, metal ions are dissolved out therefrom in living bodies and affect a toxic action to bone cells around the implant. Furthermore, the bone-formation is obstructed probably because of too large a thermal conductivity of the metallic implant. Among the metallic materials, titanium and tantalum are particularly superior in a corrosion-resistance and hence have been employed as fixing plates for skulls or fractured parts of bones and implants for jawbones since about 1940, but these are not necessarily satisfactory.

To the contrary, ceramic materials show generally a good affinity to bones, and hence tissues penetrate into fine pores of the ceramic materials to afford a strong fixation, without reaction between the ceramic material and the tissue. Besides, they are also excellent in durability, that is, they are resistant to corrosion decomposition. On the other hand, they posses a poor impact strength.

There has been proposed an implant having the characteristics of both of metallic materials and ceramic materials, i.e. an implant prepared by thermally spraying a ceramic material onto the surface of a metallic core material (cf. Japanese Patent First Publication Nos. 14095/1977, 82893/1977, 28997/1978 and 75209/1978). In these methods, however, a self-bonding type bonding agent is used in order to improve the adhesion of the ceramic coating layer. The bonding agent has a problem in that it contains nickel, chromium, etc. which dissolve out in living bodies and exhibit toxicity to living bodies.

SUMMARY OF THE INVENTION

The present inventors have conducted intensive studies as so to developed improved endosseous implants which have excellent impact strength and hence resistance to cracking, while keeping the excellent properties of ceramic materials and preventing the dissolving out of toxic metal ions. The present inventors, therefore, have now found that the desired endosseous implants can be prepared by thermally spraying a ceramic material onto a metallic core material having a rough surface.

Accordingly, an object of this invention is to provide an improved endosseous implant which has excellent characteristics of both a metallic material and a ceramic material and does not dissolve out toxic metal ions.

Another object of an invention is to provide an improved method for producing the excellent endosseous implant by thermally spraying a ceramic material onto a metallic core material having a rough surface, i.e. having a maximum surface roughness of 15 to 100 $\mu$m.

A further object of the invention is to provide a method for producing an excellent endosseous implant by thermally spraying titanium hydride onto the surface of a metallic core material for making the surface thereof rough at a maximum surface roughness of 15 to 100 $\mu$m and thermally spraying a ceramic material thereon. Another object of the invention is to provide a method for producing the excellent endosseous implant by making the metallic core material rough by etching with an acid to a maximum surface roughness of 15 to 100 $\mu$m, and then thermally spraying a ceramic material thereon. Yet another object of an invention is to provide a method for producing the endosseous implant without using any bonding agent which contains toxic metal ions.

These and other objects and advantages of the present invention will be apparent to those skilled in the art from the following description.

DETAILED DESCRIPTION OF THE INVENTION

Figure 1:
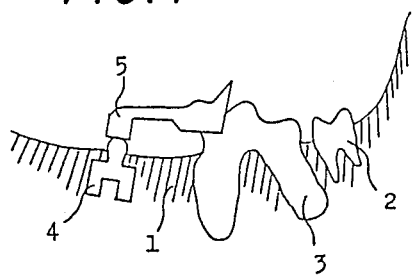
FIG. 1 is a schematic view of an embodiment of the endosseous implant for the lower jawbone of dog, wherein 1 represents the lower jawbone, 2 and 3 are natural teeth, 4 is an artificial tooth root and 5 is an artificial tooth crown attached on the artificial tooth root 4.
Figure 2A:
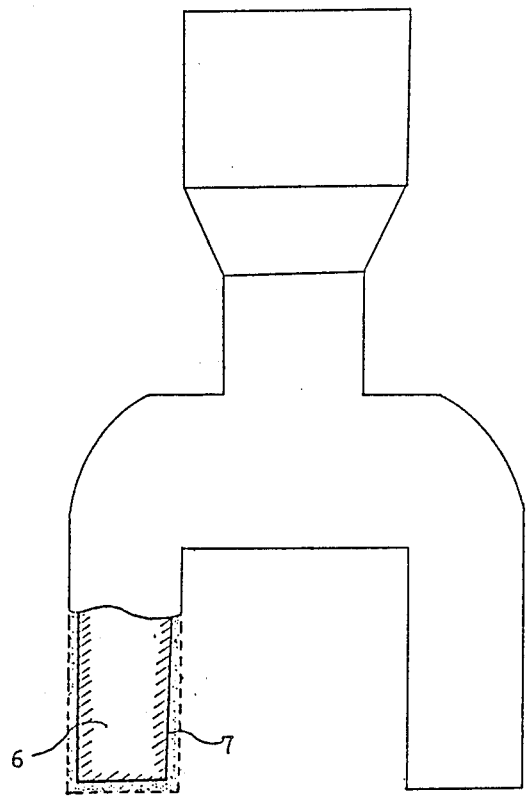
FIG. 2 is a partial schematic view of an embodiment of the endosseous implant for jawbone of a blade type according this invention, and (A) is a front view thereof and (B) is a side view thereof, wherein 6 represents a metallic implant (core material) and 7 is a ceramic layer containing unopened pores which do not reach the metal surface.
Figure 2B:
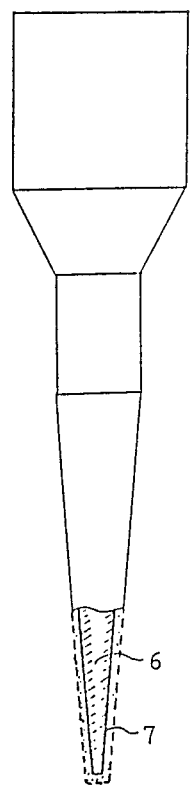

According to the present invention, as is shown in FIG. 2, a ceramic coating is applied to the surface of a metallic implant core material so as to obtain an implant which is hardly breakable with a sufficient impact strength and acting to the surrounding bone tissues in a similar manner as ceramic materials.

The metallic core materials used in this invention include any conventional materials which have usually been used as artificial materials for bones, joints and tooth roots which do not exhibit harmful effects on living bodies and possess an appropriate mechanical strength, for example, cobalt-chromium alloys, stainless steels, titanium, titanium alloys, tantalum, zirconium, and the like. Among these materials, the preferred ones are titanium, titanium alloys, zirconium and tantalum in view of their excellent corrosion resistance. Most preferred are titanium and titanium alloys (e.g. 6% Al-4% V-Ti, etc.) in view of their excellent processability and safety.

The ceramic materials used in this invention include hydroxyapatite, calcium phosphate, aluminum oxide, zirconium oxide, titanium oxide, and the like, which may be used alone or in combination of two or more thereof. In order to control the pores in the ceramic layer, a porcelain may be applied by thermally spraying together with the ceramic material or by baking on the ceramic coating layer. For such a purpose, there can be used porcelains such as Dentin and Enamel. Among the ceramic materials, preferred ones are hydroxyapatite and aluminum oxide in view of thier excellent affinity with living bodies. A combination of hydroxyapatite and aluminum oxide is particularly suitable because it is most intimate with living bodies.

The endosseous implants of this invention can be produced in the following manner.

The metallic material is formed into the desired shape by conventional methods, such as cutting, casting, forging, punching, electro arc machining, laser-processing, and powdered metal techniques. The surface of the metallic core materials thus formed is made rough to a specific maximum surface roughness. The maximum surface roughness of the metallic core materials is in the range of 15 μm to 100 μm. When the maximum surface roughness is smaller than 15 μm, the thermally sprayed ceramic coating layer demonstrates insufficient adhesion. On the other hand, when it is larger than 100 μm, it is disadvantageously difficult to form a thin uniform layer of the ceramic coating. The most suitable maximum surface roughness is in the range of 20 to 60 μm in view of the adhesion and uniformity of the coating layer.

In order to make the surface rough the metallic core materials rough, various methods are applicable, for example, mechanical methods such as grinding, sandblasting, grit blasting, etc.: chemical etching such as treatment with an acid or alkali: electrolytic etching: forming of a titanium layer having a rough surface by thermally spraying titanium hydride powder: and the like. Among these methods, preferred ones are blasting, chemical etching, and forming of a titanium layer having rough surface, because the ceramic material can easily bite into the rough surface. The chemical etching is usually carried out by using mineral acids, such as sulfuric acid, hydrochloric acid, hydrofluoric acid, which are used alone or in a combination of two or more thereof. When the blasting and etching with an acid are combined, particularly, when the metallic core material is first subjected to blasting and then to etching with an acid, the core material demonstrates extremely preferable adhesion of the coating layer. Furthermore, when the metallic core materials are coated with titanium having a rough surface by thermally spraying titanium hydride powder, it is preferable to previously subject the materials to the above surface-roughing treatments, such as mechanical treatment (e.g. grinding, sandblasting, grit balsting), chemical etching with an acid or alkali, electrolytic etching. The thermal spraying of titanium hydride is preferably carried out by thermal plasma spraying. The particle size of titanium hydride is not particularly limited, but is preferably in the range of 10 to 100 μm. The titanium coating layer does substantially not dissolve out any harmful metal ion, contrary to the self-bonding type bonding agent containing metals which are easily dissolved out in living bodies.

In the thermal spraying of ceramic materials, the portion, which is not coated with the ceramic material is previously masked by an appropriate means, for instance, application of a marking ink, an aluminum adhesive tape, etc., prior to the treatment for making the surface rough. The thermal spraying of the ceramic material is also preferably carried out by a thermal plasma spraying apparatus. Some portions of the endosseous implants, for instance, the ceramic coating layer in artificial joints, are required to have high smoothness. In such a case, a porcelain is coated onto the surface and the coated product is repeatedly calcined in a vacuum furnace.

In the endosseous implants of this invention, the thickness of the ceramic coating layer which optionally contains the porcelain is not particularly limited, but is preferably in the range of 10 to 200 μm.

This invention is illustrated by the following Examples but should not be construed to be limited thereto.

EXAMPLE 1

A core material for an endosseous implant is prepared by using a titanium material (JIS, second class of material) in the following manner, i.e. by cutting and grinding the titanium material by electro arc machining.

The metallic core material for the implant is grit-blasted with a blast apparatus (a mammoth type venti-blast apparatus, manufactured by Metco Inc., England: blasting agent: Metcolite VF, manufactured by Metco Inc.; pressure: 30 psi). The thus-blasted material has a maximum surface roughness of 10 μm.

The blasted core material is dipped in 30% sulfuric acid solution at 50° C. for 72 hours to effect etching. After the etching, the core material has a maximum surface roughness of 50 μm.

Under generation of argon-hydrogen-plasma jet flame (ARC electric current 500 Amp) by a plasma spray apparatus (6MM-630 type, manufactured by Metco Inc., equipped with an electric power supplier), a ground mixture of hydroxyapatite (particle size: 10–100 μm, 80% by weight) and aluminum oxide (WA #120, manufactured by Nippon Kenmazai K.K., 20% by weight) is thermally sprayed to form a coating layer having a thickness of about 150 μm in average. The thermally sprayed coating layer has excellent adhesion, and even when the product is subjected to a bending processing at an angle of 160°, the coating layer is not peeled off.

The product obtained above was tested as follows:

The implant was embedded into the lower jawbone of a dog. After 3 months, it was observed by X-ray fluoroscopy. As a result, there was confirmed formation of dense bone around the implant.

EXMAPLE 2

A core material for an endosseous implant is prepared by using a titanium material (JIS, second class of material) in the following manner, i.e. by cutting and grinding the titanium material by electro arc machining.

The metallic core material for the implant is grit-blasted with a blast apparatus (a mammoth type venti-blast apparatus, manufactured by Metco Inc., England:

blasting agent: Metcolite VF, manufactured by Metco Inc.; pressure: 30 psi). The thus-blasted material has a maximum surface roughness of 10 μm.

Under generation of argon-hydrogen-plasma jet flame (ARC electric current 500 Amp) by a plasma spray apparatus (6MM-630 type, manufactured by Metco Inc., equipped with an electric power supplier), titanium hyride powder (Powder No. XP-1157, manufactured by Metco Inc.) is thermally sprayed, as the first coating layer, onto the blasted core material to form a first coating layer of about 50 μm in thickness on the whole surface thereof. As the second coating layer, a mixture of hydroxyapatite (particle size: 10–100 μm, 80% by weight) and aluminum oxide (WA #120, manufactured by Nippon Kenmazai K.K., 20% by weight) is thermally sprayed to form a coating layer having an average thickness of about 150 μm. The thermally sprayed coating layer has excellent adhesion, and even when the product is subjected to bending processing at an angle of 160°, the coating layer is not peeled off.

The product obtained above was tested as follows:

The implant was embedded into the lower jawbone of a dog. After 3 months, it was observed by X-ray fluoroscopy. As a result, there was confirmed the formation of dense bone around the implant.

REFERENCE EXAMPLE

A core material for an endosseous implant is prepared by using the same titanium material in the same manner as described in Example 1. The core material is subjected to grid blasting likewise, but is not subjected to etching. The material has a maximum surface roughness of 10 μm which is about 1/5 of that of the core material before thermal spraying in Example 1.

The blasted core material is thermally sprayed with a mixture of hydroxyapatite and aluminum oxide in the same manner as in Example 1 to give a coating layer having an average thickness of about 150 μm in average. The resulting product has significantly inferior adhesion of the coating layer and the coating layer is easily peeled off even by a light impact. Thus, this product cannot be used as an endosseous implant.

What is claimed is:

1. A method for producing an endosseous implant which comprises: thermally spraying titanium hydride onto a surface of a metallic core material to make the surface of the metallic core material rough to a maximum surface roughness of 15 to 100 μm; and then thermally spraying a ceramic material onto the roughened surface.

2. The method of claim 1, wherein the metallic core material is selected from the group consisting of cobalt-chromium alloys, stainless steel, titanium, titanium alloys, tantalum and zirconium.

3. The method according to claim 1, wherein the surface of the metallic core material is made rough by subjecting the core material to blasting or etching with an acid and then thermally spraying titanium hydride onto the surface thereof.

4. The method according to claim 1, wherein the metallic core material has a maximum surface roughness of 20 to 60 μm.

5. The method according to claim 1, wherein the ceramic material for thermal spray coating comprises hydroxyapatite.

6. The method according to claim 1, wherein the ceramic material for thermal spray coating comprises a mixture of hydroxyapatite and aluminum oxide.

7. A method for producing an endosseous implant which comprises: blasting a surface of a metallic core material selected from the group consisting of titanium and a titanium alloy; thermally spraying titanium hydride having a particle size of 10 to 100 μm onto the surface of the blasted metallic core material to make the surface of the core material rough to a maximum surface roughness of 15 to 100 μm; and thermally spraying a ceramic material selected from the group consisting of alumina, hydroxyapatite and a mixture of alumina and hydroxyapatite onto the surface of the resulting core material, thereby forming a layer of the ceramic material of 10 to 200 μm in thickness on the surface.

8. A method for producing an endosseous implant which comprises: thermally spraying titanium hydride onto a surface of a metallic core material to make the surface of the metallic core material rough to a maximum surface roughness of 15 to 100 μm; and then thermally spraying a ceramic material onto the roughened surface without using any bonding agent which contains toxic metal ions.

* * * * *